United States Patent [19]

O'Lenick, Jr.

[11] Patent Number: 5,098,746

[45] Date of Patent: Mar. 24, 1992

[54] FIBER TREATMENT PROCESS UTILIZING SILANOL WAXES

[75] Inventor: Anthony J. O'Lenick, Jr., Lilburn, Ga.

[73] Assignee: Siltech Inc., Norcross, Ga.

[21] Appl. No.: 681,728

[22] Filed: Apr. 8, 1991

Related U.S. Application Data

[63] Continuation-in-part of Ser. No. 470,224, Jan. 25, 1990, Pat. No. 5,051,489.

[51] Int. Cl.$^5$ ............................................. B05D 3/02
[52] U.S. Cl. ................................. 427/387; 424/70; 424/59; 427/389; 427/389.9; 427/391; 428/446; 428/484
[58] Field of Search .................. 424/78; 427/387, 389, 427/389.9, 391; 428/447, 452, 446, 484

[56] References Cited

U.S. PATENT DOCUMENTS

| | | | |
|---|---|---|---|
| 3,257,343 | 6/1966 | Glaser et al. | 528/26.5 |
| 3,583,885 | 6/1971 | Preston | 528/26.5 |
| 4,125,498 | 11/1978 | Blount | 528/26.5 |
| 4,608,421 | 8/1986 | Lin | 528/26 |
| 4,683,271 | 7/1987 | Lin et al. | 528/26 |

Primary Examiner—Michael Lusignan

[57] ABSTRACT

The invention discloses novel silanol waxes and applications thereof. Compounds of the invention by virtue of their silanol fatty ester group are waxy lubricious solids which provide outstanding lubrication and hydrophobicity when applied to surfaces like fiber, hair, skin or paper. The compounds of the present invention are prepared by reacting a silanol compound with a fatty carboxylic and or polycarboxylic acid, ester or anhydride.

9 Claims, No Drawings

FIBER TREATMENT PROCESS UTILIZING SILANOL WAXES

This application is a continuation in part of Ser. No. 07/470,224 filed 01/25/1990, now U.S. Pat. No. 5,051,489.

BACKGROUND OF THE INVENTION

1. Field of the Invention

The present invention relates to novel compounds and compositions containing and applications of a series of novel silanol fatty esters. The compositions provide outstanding lubrication, and hydrophobicity to a variety of substrates. The compositions of the present invention contain novel waxy solids which melt under pressure to give a clear liquid lubricating oil. The esterification by which the compounds are prepared is the reaction of a silanol, a hydroxy containing silicone polymer, and a fatty acid or polycarboxylic acids.

2. Arts and Practices

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quats are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the siloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

In many applications, there is a strong desire to obtain a solid wax which can be used in applications were a spread on application is of interest. These applications include personal care applications like antiperspirants and skin creams. Unfortunately most silicone derivatives are liquid to very low temperatures. Attempts to overcome this deficiency have been made by reacting stearyl alcohol with a chloro silane to obtain the following product marketed by Dow Corning;

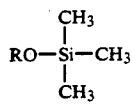

The difficulty with the use of this material is that a large excess (50% by weight) of the alcohol needs to be added to get a product which is free of the irritating chlorosilane raw material. When such an excess is used the product behaves functionally more like the stearyl alcohol than like a silicone compound. Additionally, the compound is not polymeric, hence the superior lubrication and hydrophobicity enhancements which can be achieved by dimethylpolysiloxane is not obtainable with these compounds.

Many attempts have been made to overcome these problems and get a truly lubricious silicone wax.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

THE INVENTION

Object of the Invention

It is the object of the present invention to provide compositions containing novel silanol fatty ester compounds and processes for their utilization.

It is another objective of the current invention to provide processes for the utilization of silanol esters in personal care and textile applications to render softness and lubrication to the substrates being treated. The superior antistatic properties are an important benefit, since this is a major aspect of consumer perception of softness in consumer and industrial laundry applications. Lubrication has been a property which is purported to effect garment life. Application of the compounds of the invention can be from solvent, aqueous dispersion or solution, or applied neat in these processes. The compounds of the current invention make outstanding napping lubricants were a waxy material which liquefies under application of pressure is desirable.

One specific application of the compounds of the present invention is as gloss additive applied to the hair. These waxes liquefy when rubbed into the hands and give a gloss when applied to the hair. These materials are nonirritating to skin and eyes and nontoxic.

Another personal care application for the waxes of the present invention is as a solid base for the suspension of pigments and other particulate materials. One major application area is the suspension of titanium dioxide into the wax. Not only is the wax a hydrophobic base for this application, but it does not distort the structure of the titanium dioxide. This results in no negative effect upon the sun screen protection provided by the titanium dioxide.

The waxes of the present invention are also useful in the lubrication of thread. Prior practice was to use paraffin wax cast into discs, or applied at elevated temperatures. The compounds of the present invention are liquefy with pressure and give a uniform coating of a non toxic lubricant to thread. The hard paraffin waxes have a tendency to break the thread fibers.

It is also envisioned that the compounds of the present invention can be used for waterproofing paper, specifically boxes. This is particularly important for boxes which are placed in a freezer.

SUMMARY OF THE INVENTION

The present invention relates to processes for the utilization of novel silanol fatty ester compounds. The compounds by virtue of the silanol ester group form effective surface modifying finishes. The compounds of the present invention are substantive to paper, hair, skin, cellulosic and synthetic fibers as well as metal surfaces and plastic polymers.

The compounds of this invention are silanol esters made by the esterification of a fatty acid and/or polycarboxylic acid, ester or anhydride with a silanol compound. The compounds of the present invention conform to the following structure;

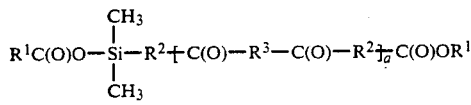

$R^2$ is

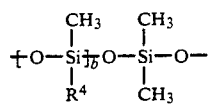

$R^1$ is alkyl having 6 to 30 carbon atoms;
$R^3$ is selected from —(CH$_2$)$_c$—, or —(CH$_2$)$_d$—CH=CH—(CH$_2$)$_e$—;

a is an integer from 0 to 20;
b is an integer from 1 or 200;
c, d and e are independently integers from 1 to 10;
$R^4$ is alkyl having from 1 to 18 carbon units or aryl $C_6H_5$.

PREFERRED EMBODIMENTS

The process of conditioning the various substrates utilizes the compounds of the present invention in concentrations ranging from 0.01 and 20.0%. Preferred concentrations range from 0.1 and 10.0%, with the most preferred concentration ranging from 1.0 and 8.0%.

One preferred material for the preparation of the compounds of the present invention is when a is 0, and R is alkyl having between 16 and 20 carbon atoms. It is at this concentration that the most substantivity is achieved.

One compound of major interest is when a is 0 and R is alkyl having 18 carbon atoms (derived from stearic acid). Another compound is derived from 12 hydroxystearic acid.

EXAMPLES

The compounds of the present invention are prepared by the reaction of a silanol compound and a fatty acid or polyacid. Examples of suitable reactants are as follows;

REACTANTS

| Fatty Acids | Formula | Molecular Weight |
|---|---|---|
| Lauric | C12 (Saturated) | 200 |
| Myristic | C14 (Saturated) | 228 |
| Stearic | C18 (Saturated) | 284 |
| Oleic | C18 (Unsaturated) | 282 |
| Linoleic | C18 (Unsaturated) | 280 |
| Adipic Acid | HO(O)C(CH2)$_4$C(O)OH | 146 |
| Succinic Acid | HO(O)C(CH2)$_2$C(O)OH | 118 |
| Dodecanedioic Acid | HO(O)C(CH2)$_{10}$C(O)OH | 230 |

SILANOL COMPOUNDS

Silanol compounds are well known and are marketed in the trade under many names. The compounds conform to the following generic structure;

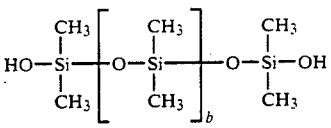

b is an integer from 1 to 200.

Compounds of the following structure are available from Siltech Inc. Norcross Ga. and are marketed under the Siltech S series trade name shown;

| Name | Molecular Weight |
|---|---|
| Siltech S 701 | 1,000 |
| Siltech S 706 | 6,000 |
| Siltech S 710 | 10,000 |
| Siltech S 750 | 50,000 |
| Siltech S 790 | 86,000 |

GENERAL REACTION CONDITIONS

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titanates, organo tin compounds, organo zinc compounds, zinc oxide, magnesium oxide, calcium oxide, etc. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

The reaction can be run with either a stiochiometric amount of the fatty acid. However, it is recommended that an excess of about 1 to 5% of one acid be employed.

DIESTER EXAMPLES

EXAMPLE 1

Into a suitable round bottom, three neck flask equipped with a Dean Stark trap, a thermometer and a nitrogen sparge is added 284.0 grams of stearic acid, 0.25% by weight of the total batch charged of stannous oxylate and 5,000 grams of Siltech S 710. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is a white wax and is used without additional purification.

The compounds of the produced by the Diester Examples have the following structure;

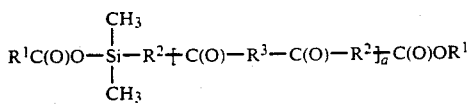

where a is 0.

EXAMPLES 2-12

Example 1 is repeated only this time substituting the specified number of grams of the fatty acid specified for the stearic acid and the specified type and number of grams of silanol compound as shown below;

| Example | Fatty Acid | | Silanol Compound | |
|---|---|---|---|---|
| | Type | Grams | Type | Grams |
| 2 | Lauric | 200.0 | S 701 | 500.0 |
| 3 | Myristic | 228.0 | S 701 | 500.0 |
| 4 | Stearic | 284.0 | S 701 | 500.0 |
| 5 | Hydroxy Stearic | 282.0 | S 701 | 500.0 |
| 6 | Lauric | 200.0 | S 706 | 3,000.0 |
| 7 | Myristic | 228.0 | S 706 | 3,000.0 |
| 8 | Stearic | 284.0 | S 706 | 3,000.0 |
| 9 | Myristic | 228.0 | S 710 | 5,000.0 |
| 10 | Stearic | 284.0 | S 710 | 5,000.0 |
| 11 | Oleic | 282.0 | S 750 | 25,000.0 |
| 12 | Stearic | 284.0 | S 790 | 45,000.0 |

POLYMERICS

EXAMPLE 13

Into a suitable round bottom, three neack flask equipped with a Dean Stark trap, a thermometer and a nitrogen sparge is added 254.0 grams of lauric acid, 7.3 grams of adipic acid, 0.25% of total weight of the batch of stannous oxylate and 500 grams of Siltech S 701. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is a white wax and is used without additional purification.

The compunds of the produced by the Polymeric Examples have the following structure;

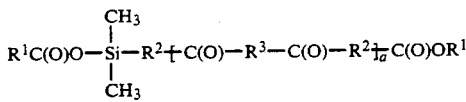

where a is greater than 0.

EXAMPLE 14-23

Example 13 is repeated only this time substituting the specified number of grams of the fatty acid specified for the lauric acid and the specified type and number of grams of diacid and the specified type and number of grams of silanol compound as shown below;

| Example | Fatty Acid | | Silanol Compound | |
|---|---|---|---|---|
| | Type | Grams | Type | Grams |
| 14 | Myristic | 205.0 | S 701 | 500.0 |
| | Dodecanedioic | 11.5 | | |
| 15 | Stearic | 227.0 | S 701 | 500.0 |
| | Adipic | 14.6 | | |
| 16 | Oleic | 197.0 | S 701 | 500.0 |

| Example | Fatty Acid | | Silanol Compound | |
|---|---|---|---|---|
| | Type | Grams | Type | Grams |
| | Succinic | 17.7 | | |
| 17 | Lauric | 190.0 | S 706 | 3,000.0 |
| | Dodecanedioic | 5.7 | | |
| 18 | Myristic | 216.6 | S 706 | 3,000.0 |
| | Adipic | 3.7 | | |
| 19 | Stearic | 142.0 | S 706 | 3,000.0 |
| | Adipic | 36.5 | | |
| 20 | Myristic | 193.8 | S 710 | 5,000.0 |
| | Succinic | 7.5 | | |
| 21 | Stearic | 197.0 | S 710 | 5,000.0 |
| | Adipic | 1.9 | | |
| 22 | Oleic | 253.0 | S 750 | 25,000.0 |
| | Dodecanedioic | 11.5 | | |
| 23 | Stearic | 227.0 | S 790 | 45,000.0 |
| | Dodecanedioic | 23.0 | | |

APPLICATIONS EXAMPLES

Applications of the Compounds of The Invention

Compounds of this invention were compared to standard compounds commercially available using AATCC Test Method 117 - 1979. The color fastness heat test uses a 400 F. (205 F.) hot iron which is applied for 60 and 180 seconds. The color is rated on a 1-5 basis for yellowness, (5 being the most yellow).

| Compound | Yellowness |
|---|---|
| Alkaquat T (Imidazoline Quat) | 4 |
| Alkaquat DAET 90 (Amido Quat) | 5 |
| Example #4 | 1 |
| Example #19 | 2 |

As can be seen the compounds of the present invention are non-yellowing softeners when compared to standard softeners.

LUBRICATION

FRICTIONAL PROPERTIES

| PRODUCT | DESCRIPTION (70 F.) | LUBRICATION DATA[1] Coefficient of Friction FIBER/METAL | |
|---|---|---|---|
| | | 100 | 300 |
| | | (m/min.) | |
| Butyl Stearate | White Liquid | 0.17 | 0.21 |
| Tridecyl Stearate | Clear Liquid | 0.25 | 0.27 |
| Example 4 | White Wax | 0.06 | 0.01 |
| Example 19 | White Wax | 0.07 | 0.02 |
| Ditallowdimethyl benzalkonium chloride | Tan solid | 0.35 | 0.35 |
| Ditridecyl adipate | Clear Amber Liquid | 0.28 | 0.29 |
| Untreated Fiber | | 0.98 | 1.01 |

[1]Rothchild F Meter, Fiber; 150 denier polyester, Temperature: 72 F., Relative humidity: 60%

As can be easily seen the compounds of the present invention are excellent lubricants.

WET COMB OUT TEST

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearydimethylbenzyl ammonium chloride) range from 12-14 seconds.

| Rinse Conditioner (Wet Comb Out Test) | |
|---|---|
| Product | Time in Seconds |
| Example #10 | 11 |
| Example #22 | 13 |
| Stearyldimethylbenzyl ammonium chloride | 12 |

As can be seen, the compounds of the invention give significant conditioning properties to hair makes them prime candidates for cosmetic as well as textile and other related applications. The following examples are typical formulations which utilize the compounds of the present invention;

DEODORANT FORMULATION

The compounds of the invention can be utilized to formulate deodorant sticks and related products. The silanol ester wax of this invention are less volatile than the cyclic silicones commonly used and can be used to replace stearyl alcohol in many formulations. Superior feel and lubrication are achieved. A typical formulation is;

| Material | % |
|---|---|
| Stearyl alcohol | 20.0 |
| Example 4 | 20.0 |
| Exxal 20 | 10.0 |
| Cyclic silicones | 5.0 |
| Ethanol | 35.0 |
| 1,2 propylene glycol | 10.0 |

ROUGE

The compounds of the invention can be utilized to formulate rouge and related products. A typical formulation is;

| Material | % |
|---|---|
| Stearyl Alcohol | 7.0 |
| Example 20 | 5.0 |
| Exxal 20 | 5.0 |
| Ethanol | 5.0 |
| Magnesium Stearate | 2.0 |
| Kaolin | 15.0 |
| Starch | 5.0 |
| Magnesium carbonate | 2.0 |
| Talc | 44.0 |
| Titanium dioxide | 5.0 |
| Powder brown (color) | 5.0 |

EYESHADOW

The compounds of the invention can be utilized to formulate eyeshadow products. A typical formulation is;

| Material | % |
|---|---|
| Stearyl Alcohol | 55.0 |
| Example 12 | 20.0 |
| Ozokerit 70-72 | 15.0 |
| Color (Ariabel 300 403 | 10.0 |

LIP STICK FORMULATION

The compounds of this invention make outstanding bases for the preparation of lipstick products. The lipsticks made with these materials have outstanding slip and provide lubrication and emmoliency properties to the stick. A typical formulation is;

| Material | % |
|---|---|
| Stearyl alcohol | 40.0 |
| Example 4 | 40.0 |
| Exxal 20 | 10.0 |
| Color | 5.0 |
| Titanium dioxide | 5.0 |

LIPCREAM

By replacing the C-20 guerbet alcohol with a guerbet citrate ester (Siltech CE 2000) and altering the ratio of components a lipcream can be formulated;

| Material | % |
|---|---|
| Stearyl alcohol | 40.0 |
| Example 4 | 40.0 |
| Siltech CE-2000 | 15.0 |
| Color | 3.0 |
| Titanium dioxide | 2.0 |

DRYER SHEET SOFTENER

The compounds of the present invention can be incorporated into drier sheet softener formulations to improve fiber to metal lubrication (antistat), fiber to fiber lubrication (hand and softness) without adversely effecting the melting point of the sheet. Traditional silicone compounds have not been widely used in these applications because of their liquidity, which alters the melting point properties of the sheet.

| Material | % |
|---|---|
| Stearyl imidazoline quat | 60.0 |
| Example 15 | 20.0 |
| Stearyl acid 8 mole ethylene oxide | 20.0 |

FURNITURE AND AUTOMOTIVE WAX

The compounds of the present invention can be incorporated into wax formulations for furniture and automotive applications. Their high lubrication properties as well as their being solid at ambient temperatures makes them excellent wax bases. The property of liquification under pressure also contributes to the functionality.

LAUNDRY DETERGENT

The compounds of the invention can be added to powdered detergents to obtain a detergent/softener/antistat package in one compound.

PERSONAL CARE

Sun Screen Base

The compounds of the present invention can be applied to the skin to give breathable (i.e. oxygen permeable) hydrophobic films. Consequently these materials are useful in formulating sun screen products with both organic and inorganic components. Suitable inorganic components are micro titanium dioxide. Surprisingly, the titanium dioxide is dispersible in the novel molten wax at concentrations of between 0.5% and 50% by weight. A 20% dispersion of micro titanium dioxide in Example 4 wax, when applied to the skin gives a uniform transparent hydrophobic film which has a sun protection factor of 15.

HAIR GLOSS ADDITIVE 1.0 grams of wax example 4 is applied to clean dry hair after rubbing into the palms. The hair is then brushed. A high sheen nongreasy finish results.

What is claimed:

1. A process of treating fibrous substrates which comprises contacting the substrate with an effective conditioning amount of a compound conforming to the following structure;

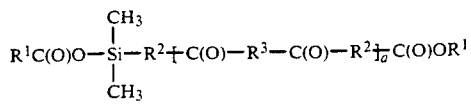

$R^2$ is

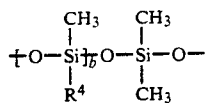

$R^1$ is alkyl having from 6 to 30 carbon atoms;
$R^3$ is selected from $-(CH_2)_c-$, or $$-(CH_2)_d-CH=CH-(CH_2)_e-;$$

a is an integer from 0 to 20;
b is an integer from 1 to 200;
c, d and e are independently integers from 1 to 10;
$R^4$ is alkyl having 1 to 18 carbon units or $C_6H_5$.

2. A process of claim 1 wherein the effective conditioning amount ranges from 0.01 and 20.0%.
3. A process of claim 1 wherein the effective conditioning amount ranges from 0.1 and 10.0%.
4. A process of claim 1 wherein a is 0, R is alkyl having 18 carbon atoms.
5. A process of claim 1 wherein said fibrous substrate is selected from hair, skin, paper, and textile fibers.
6. A process of claim 1 wherein said fibrous substrate is hair.
7. A process of claim 1 wherein said fibrous substrate is skin.
8. A process of claim 1 wherein said fibrous substrate is a textile fiber.
9. A process of claim 1 additionally containing titanium dioxide.

* * * * *